United States Patent [19]

Aono et al.

[11] Patent Number: 5,153,201
[45] Date of Patent: Oct. 6, 1992

[54] CONDENSED THIAZOLE COMPOUNDS AND USE AS PHARMACEUTICALS

[75] Inventors: Tetsuya Aono, Nagaokakyo; Masahiro Suno, Kobe; Go Kito, Yao, all of Japan

[73] Assignee: Takeda Chemical Industries, Ltd., Osaka, Japan

[21] Appl. No.: 658,021

[22] Filed: Feb. 22, 1991

[30] Foreign Application Priority Data

Feb. 23, 1990 [JP] Japan ................................ 2-44095
Sep. 27, 1990 [JP] Japan ................................ 2-259656

[51] Int. Cl.$^5$ .................. A61K 31/435; C07D 513/04
[52] U.S. Cl. .................. 514/301; 514/234.2; 514/253; 514/254; 514/367; 544/127; 544/405; 546/114; 548/153
[58] Field of Search ............. 546/114; 548/153; 544/127, 405; 514/301, 367, 234.2, 253, 254

[56] References Cited

FOREIGN PATENT DOCUMENTS 0331960 3/1989 European Pat. Off. .
0351856 1/1990 European Pat. Off. .
3211973 11/1982 Fed. Rep. of Germany .
2102279 4/1972 France .

OTHER PUBLICATIONS

Ivan A. Natchev, "Phosphono and Phosphino Analogues and Derivatives of the Natural Aminocarboxylic Acids and Peptides 1. Synthesis and Enzyme-Substrate Interactions of N-Phosphono-, and N-Phosphinomethylated Cyclic Amides", Synthesis, No. 12, Dec. 1987, pp. 1079-1084.
Chemical Abstracts, vol. 50, 14753a (1956); Fridman, Zhur. Obshchei, vol. 26, pp. 864-867 (1956).

Primary Examiner—Bernard Dentz
Attorney, Agent, or Firm—Wegner, Cantor, Mueller & Player

[57] ABSTRACT

A novel condensed thiazole derivative of the formula [I]:

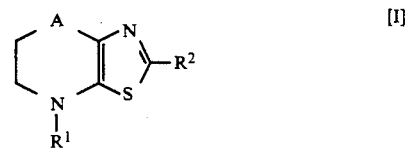

wherein A is a single bond or $CH_2$; $R^1$ is hydrogen atom, or an optionally substituted aliphatic, carboxylic acyl or sulfonic acyl group; and $R^2$ is hydrogen atom, or an optionally substituted aromatic cyclic or aliphatic group, or a salt thereof. The compound [I] is useful for medicines for preventing and treating various diseases such as cancer, arterial sclerosis, hepatopathy, cerebrovascular diseases, inflammatory and the like. A process of the compound of the formula [I] or a salt thereof and a pharmaceutical composition comprising the compound of the formula [I] or a pharmaceutically acceptable salt thereof as an active component are also disclosed.

22 Claims, No Drawings

CONDENSED THIAZOLE COMPOUNDS AND USE AS PHARMACEUTICALS

FIELD OF THE INVENTION

The present invention relates to novel condensed thiazole derivatives and salts thereof, their production and pharmaceutical compositions containing the same as an active component. More particularly, it relates to novel lipoperoxide formation inhibitors and lipoxygenase inhibitors, which are useful as medicines for preventing and treating various diseases such as cancer, arterial sclerosis, hepatopathy, cerebrovascular diseases, inflammatory and the like.

BACKGROUND OF THE INVENTION

As it has become evident that the formation of a lipoperoxide in the body and a concomitant radical reaction have various harmful effects on the living body through membrane disorders, enzymatic disorders and the like, various attempts to use antioxidants and lipoperoxide formation inhibitors as medicines have been made. At present, the main lipoperoxide formation inhibitors used in the art are derivatives of natural antioxidants such as vitamin C, vitamin E and the like, and phenol derivative. However, their fundamental structural skeletons are limited and they are not necessarily satisfactory in practical use. Thus, it is requested to develop a lipoperoxide formation inhibitor having a novel structure so that it can be widely utilized in the medicinal field.

Under these circumstances, the present inventors synthesized a number of novel compounds and tested their lipoperoxide formation inhibitory activities, respectively. As a result, the present inventors found that certain thiazolo[5,4-b]azepine derivatives had antioxidation activity and lipoperoxide inhibitory activity, and filed a patent application (EP-A-0 351 856). Then, the present inventors further intensively studied to find out additional novel compound having the above activities. As a result, the present inventors have succeeded in the synthesis of the novel condensed thiazole derivatives of the formula [I] shown hereinafter and salt thereof. Further, it has been found that such novel compounds have activities useful for medicines, for example, strong lipoperoxide formation inhibitory activity, inhibition activity of 12-hydroxyheptadecatrienic acid (hereinafter abbreviated as HHT) and lipoxygenase, leukotriene $D_4$ ($LTD_4$) receptor antagonistic activity and the like. Thus, the present invention has been completed.

OBJECTS OF THE INVENTION

The main object of the present invention is to provide novel compounds having a lipoperoxide formation inhibitory activity.

This object as well as other objects and advantages of the present invention will become apparent to those skilled in the art from the following description.

SUMMARY OF THE INVENTION

According to the present invention, there is provided a novel condensed thiazole derivative of the formula [I]:

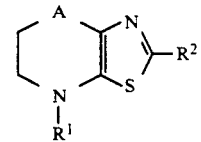

wherein A is a single bond or $CH_2$; $R^1$ is hydrogen atom, or an optionally substituted aliphatic, carboxylic acyl or sulfonic acyl group; and $R^2$ is hydrogen atom, or an optionally substituted aromatic cyclic or aliphatic group, or a salt thereof.

The present invention also provides a process for producing the compound of the formula [I] or a salt thereof and a pharmaceutical composition comprising the compound of the formula [I] or a pharmaceutically acceptable salt thereof as an active component.

DETAILED DESCRIPTION OF THE INVENTION

In the formula [I], the aliphatic group represented by $R^1$ may be a saturated or unsaturated group and examples thereof include alkyl group, alkenyl group and alkynyl group. The alkyl group may be a straight, branched or cyclic group. Among the alkyl groups, a lower alkyl group having 1 to 6 carbon atoms is preferred and examples thereof include methyl, ethyl, propyl, i-propyl, butyl, i-butyl, t-butyl, pentyl, hexyl, cyclopropyl, cyclobutyl, cyclopentyl and the like. As the alkenyl group represented by $R^1$, in general, that having 2 to 6 carbon atoms is preferred and examples thereof include vinyl, allyl, propenyl, i-propenyl, 2-butenyl, 2,4-butadienyl, 1,3-butadienyl, 2-pentenyl, 2,4-pentadienyl and the like. As the alkynyl group represented by $R^1$, in general, that having 2 to 6 carbon atoms is preferred and examples thereof include ethynyl, 2-propynyl and the like. The substituent by which these aliphatic groups are optionally substituted may be any group which is normally used for medicines and examples thereof include hydroxyl; $C_{1-3}$ alkoxy such as methoxy, ethoxy, n-propoxy, iso-propoxy and the like (e.g., as methoxymethyl, 1-ethoxyethyl, etc.); aryloxy such as phenoxy and the like; $C_{7-10}$ aralkoxy such as benzyloxy and the like; mercapto; $C_{1-3}$ alkylthio such as methylthio, ethylthio and the like; arylthio, preferably $C_{6-10}$ arylthio such as phenylthio, naphthylthio and the like; $C_{7-10}$ aralkylthio such as benzylthio and the like; amino (e.g., as 2-aminoethyl, etc.); mono- or di- $C_{1-3}$ alkyl substituted amino such as methylamino, ethylamino, dimethylamino and the like; halogen such as chloro, bromo, fluoro, iodo (e.g., as 2-bromoethyl, etc.); esterified carboxy such as $C_{2-5}$ alkoxycarbonyl (e.g., methoxycarbonyl, ethoxycarbonyl, etc.), benzyloxycarbonyl and the like; $C_{2-4}$ alkoxycarbonyloxy (e.g., methoxycarbonyloxy, ethoxycarbonyloxy, etc.); formyl; $C_{2-10}$ acyl such as acetyl, propionyl, benzoyl and the like; $C_{2-10}$ acyloxy such as acetoxy, propionyloxy, pivaloyloxy and the like; cyano; phthalimide; $C_{2-10}$ acylimide such as acetamide, benzamide and the like; $C_{2-5}$ alkoxycarbonylamino such as methoxycarbonylamino, ethoxycarbonylamino and the like; $C_{7-10}$ aralkoxycarbonylamino such as benzyloxycarbonylamino; cyclic amino group (e.g., pyrrolidino, morpholino, etc.); carboxyl group; carbamoyl group (hereinafter, these groups are referred to as the "group A"); and the like. Among the group A, carboxyl group, esterified carboxyl group, carbamoyl group, mono- or di-($C_{1-3}$ alkyl)amino group are preferred.

As the sulfonic acyl group represented by $R^1$, preferably, there are, for example, alkylsulfonyl group having 1 to 3 carbon atoms such as methanesulfonyl, ethanesulfonyl, propanesulfonyl and the like, and phenylsulfonyl group. Among them, the alkylsulfonyl group may be substituted with the substituent selected from the above group A. Among the substituents, mono- or di- $C_{1-3}$ alkyl substituted amino such as dimethylamino, diethylamino and the like are preferred.

In the case that the phenylsulfonyl group represented by $R^1$ has a substituent on the phenyl ring, examples of the substituent include halogen such as fluoro, chloro, bromo, iodo and the like; nitro; amino (which may be substituted with one or two $C_{1-3}$ alkyl such as methyl, ethyl and the like, $C_{2-4}$ alkenyl such as vinyl, allyl and the like, $C_{3-8}$ cycloalkyl such as cyclopropyl, cyclohexyl and the like or phenyl); sulfo; mercapto; hydroxy; sulfoxy; sulfamoyl; $C_{1-6}$ alkyl such as methyl, ethyl, propyl, isopropyl and the like (which may be substituted with amino, di-$C_{1-3}$ alkylamino such as dimethylamino, diethylamino and the like, mono-$C_{1-3}$ alkylamino such as methylamino, ethylamino and the like, halogen such as fluoro, chloro, bromo, iodo and the like, hydroxy, cyano or carboxyl); $C_{1-6}$ alkoxy such as methoxy, ethoxy, propoxy, isopropoxy and the like (which may be substituted with $C_{1-3}$ alkylthio such as methylthio, ethylthio and the like); benzyloxy; $C_{1-3}$ alkylthio such as methylthio, ethylthio and the like; $C_{1-3}$ alkylsulfonamide such as methylsulfonamide, ethylsulfonamide and the like; amidino (which may be substituted with $C_{1-3}$ alkyl such as methyl, ethyl and the like or benzyl); $C_{1-3}$ alkoxyformimidoyl such as methoxyformimidoyl, ethoxyformimidoyl and the like; methylenedioxy; $C_{1-3}$ alkylsulfonyl such as methylsulfonyl, ethylsulfonyl and the like; $C_{1-3}$ alkylsulfonylamino such as methylsulfonylamino, ethylsulfonylamino and the like; esterified carboxy such as $C_{2-4}$ alkoxycarbonyl (e.g., methoxycarbonyl, ethoxycarbonyl, etc.), benzyloxycarbonyl and the like; $C_{2-4}$ alkoxycarbonyloxy such as methoxycarbonyloxy, ethoxycarbonyloxy and the like; formyl; $C_{2-10}$ acyl such as acetyl, propionyl, benzoyl and the like; $C_{2-10}$ acyloxy such as acetoxy, propionyloxy, pivaloyloxy and the like; cyano; phthalimide; $C_{2-10}$ acylamide such as acetamide, benzamide and the like; $C_{2-4}$ alkoxycarbonylamino such as methoxycarbonylamino, ethoxycarbonylamino and the like; $C_{7-10}$ aralkoxycarbonylamino such as benzyloxycarbonylamino and the like; cyclic amino (e.g., pyrrolidino, morpholino, etc.); phenyl which may be substituted with carboxyl group, carbamoyl group, halogen such as chloro, bromo, fluoro, iodo and the like, methoxy, $C_{1-14}$ 3 alkyl (e.g., methyl, ethyl etc.) and the like (hereinafter, these groups are referred to as "group P"); and the like. Among these, hydroxyl group, $C_{1-6}$ alkoxy such as methoxy, ethoxy, propoxy, isopropoxy and the like, $C_{1-6}$ alkyl such as methyl, ethyl, propyl, isopropyl and the like, halogen such as fluoro, chloro, bromo, iodo and the like, nitro, amino, mono- or di($C_{1-6}$ alkyl)amino such as methylamino, ethylamino, dimethylamino, diethylamino and the like, $C_{1-6}$ alkylthio such as methylthio, ethylthio and the like, amidino, amino $C_{1-6}$ alkyl such as aminomethyl, aminoethyl and the like, cyano, $C_{1-6}$ alkoxycarbonyl such as methoxycarbonyl, ethoxycarbonyl and the like, $C_{1-6}$ alkoxycarbonyloxy such as methoxycarbonyloxy, ethoxycarbonyloxy and the like, phenyl, phenylamidino and alkoxyformimide such as methoxyformimide, ethoxyformimide and the like are preferred. Particularly, methyl, methoxy, chloro, fluoro, amino and the like are preferred.

As the carboxylic acyl group represented by $R^1$, in general, there is a group of the formula: $R^3CO-$ (wherein $R^3$ is an optionally substituted saturated or unsaturated aliphatic group, or an optionally substituted aromatic cyclic group).

Examples of the aromatic group represented by $R^3$ include aromatic carbocyclic group and aromatic heterocyclic group. As the aromatic carbocyclic group, for example, there are phenyl, naphthyl and the like. As the aromatic heterocyclic group, a 5 to 6 membered aromatic heterocyclic group containing 1 to 4, preferably, 1 to 2 hetero atoms such as nitrogen, oxygen, sulfur and the like is preferred. Examples of the aromatic heterocyclic group include pyridyl, furyl, thienyl, pyrazinyl, pyrrolyl, imidazolyl, isoxazolyl and the like.

Further, a group wherein the above aromatic cyclic group is condensed with the same or different aromatic cyclic group (an aromatic heterocyclic or aromatic carbocyclic group as described above) is also preferred. Examples of the condensed cyclic group include indolyl, benzimidazolyl, quinolyl, imidazopyridyl, thiazopyridyl and the like.

As the substituent by which the aromatic carbocyclic group may be substituted, for example, there is a group selected from the above group P.

Further, as the substituent by which the aromatic heterocycle group may be substituted, for example, there is a group selected from the group consisting of amino (which may be substituted with $C_{2-10}$ acyl, $C_{2-4}$ halogeno acyl, Phenyl or $C_{1-3}$ alkyl), halogen such as chloro, bromo, fluoro, iodo, and the like, nitro, sulfo, cyano, hydroxy, carboxy, oxo, $C_{1-10}$ alkyl, preferable $C_{1-6}$ alkyl such as methyl, ethyl, propyl, isopropyl and the like (which may be substituted with phenyl, halogen such as chloro, bromo, fluoro, iodo and the like, amino, hydroxy, carboxy, $C_{1-3}$ alkoxy such as methoxy, ethoxy, propoxy, isopropoxy, and the like $C_{1-3}$ alkylsulfonyl such as methylsulfonyl, ethylsulfonyl and the like, $C_{1-3}$ dialkylamino such as dimethylamino, diethylamino and the like or the like), $C_{3-6}$ cycloalkyl such as cyclopropyl, cyclopentyl, cyclohexyl and the like, $C_{1-3}$ alkoxy, $C_{2-10}$ acyl such as acetyl, propionyl, benzoyl and the like, phenyl (which may be substituted with halogen such as chloro, bromo, fluoro, iodo and the like, nitro, alkyl such as methyl, ethyl, propyl and the like, alkoxy such as methoxy, ethoxy, propoxy and the like, sulfo, hydroxy or cyano), oxo and $C_{1-10}$ alkyl-thio such as methyl-thio, ethyl-thio and the like (which may be substituted with phenyl, carboxy, $C_{1-3}$ alkoxy such as methoxy, ethoxy and the like, $C_{1-3}$ alkylsulfonyl such as methylsulfonyl, ethylsulfonyl and the like, di-$C_{1-3}$ alkylamino such as dimethylamino, diethylamino and the like or the like) (hereinafter, these groups are referred to as the "group H"). Among the above group H, $C_{1-10}$ alkyl, preferably $C_{1-6}$ alkyl such as methyl, ethyl, propyl, isopropyl and the like, amino, mono- or di-($C_{1-3}$ alkyl)amino such as methylamino, ethylamino, dimethylamino, diethylamino and the like, halogen such as chloro, bromo, fluoro, iodo and the like, amino $C_{1-3}$ alkyl such as aminomethyl, aminoethyl and the like, phenyl and the like are preferred.

The aliphatic group represented by $R^3$ may be a saturated or unsaturated group and examples thereof include alkyl, alkenyl, alkynyl and the like. Examples of the alkyl group include a higher alkyl group having not less than 7 carbon atoms such as heptyl, octyl, nonyl, decyl, undecyl, dodecyl, heptadecyl, octadecyl and the like, in addition to the above lower alkyl group represented by $R^1$. As the alkyl group represented by $R^3$, the alkyl group having 1 to 18 carbon atoms is preferred, more preferably $C_{1-4}$ alkyl group such as methyl, ethyl, propyl, isopropyl and the like.

As the alkenyl group and alkynyl group represented by $R^3$, those described above with respect to $R^1$ are preferred. As the alkenyl group and alkynyl group, those having 2 to 4 carbon atoms are particularly preferred. Examples of $C_{2-4}$ alkenyl group are vinyl, allyl, propenyl, i-propenyl, 2-butenyl and the like, and examples of $C_{2-4}$ alkynyl group are ethynyl, 2-propynyl and the like.

Examples of the substituent by which these saturated or unsaturated aliphatic groups represented by $R^3$ may be substituted include the groups of the above group A, phenyl which may be substituted with the substituent selected from the above group P, phenethylamino or benzylamino group which may have the substituent selected from the above group P on its ring, heterocyclic groups which may be substituted with the substituent selected from the above group H, and the like. Examples of the heterocyclic group include a partially or completely saturated heterocyclic group (e.g., morpholino, piperidinyl, piperidino, piperadino, pyrrolidinyl and the like), in addition to the aromatic heterocyclic group as described with respect to the aromatic cyclic group represented by $R^3$.

Examples of the aliphatic group represented by $R^2$, include saturated or unsaturated aliphatic groups described above with respect to $R^1$. Further, as the alkenyl group of the unsaturated aliphatic group represented by $R^2$, the alkenyl group having 7 to 10 carbon atoms is preferred, in addition to the lower alkenyl group as described with respect to the examples of $R^1$. Examples of the substituent by which the aliphatic group represented by $R^2$ may be substituted include the group which is the same as the substituent of the above aliphatic group represented by $R^3$ and, further, it may be substituted with oxo group and the like.

Further, as the aromatic cyclic group represented by $R^2$, for example, there are the aromatic carbocyclic group and aromatic heterocyclic group as described above with respect to $R^3$ as well as their condensed cyclic group. Further, examples of the substituent by which the aromatic carbocyclic group may be substituted include the group selected from the above group P, and examples of the substituent by which the aromatic heterocyclic group may be substituted include the group selected from the above group H, respectively.

The number of the substituents optionally contained in the group represented by $R^1$, $R^2$, $R^3$ and these substituents is 1 to 5, preferably, 1 to 3.

In the compounds of the formula [I], the compounds wherein $R^1$ is hydrogen atom, $C_{1-6}$ alkyl group which may be substituted with mono- or di- $C_{1-3}$ alkyl substituted amino, $C_{1-3}$ alkylsulfonyl or carboxylic acyl group (the acyl group is preferably acetyl group, propionyl group or the like and the methyl group and ethyl group in these groups may have the above substituents) are preferred. Particularly, the compounds wherein $R^1$ is hydrogen atom are preferred. Preferably, $R^2$ is an optionally substituted aromatic group (particularly, phenyl which is optionally substituted with $C_{1-4}$ alkyl and/or nitro), an alkenyl group having 2 to 4 carbon atoms which may be substituted with an optionally substituted aromatic cyclic group (particularly phenyl or imidazolyl, they are optionally substituted with $C_{1-4}$ alkyl group, $C_{1-4}$ alkoxy and/or $C_{6-10}$ aryl, indolyl) or an alkyl group having 1 to 4 carbon atoms which may be substituted with an optionally substituted aromatic cyclic group, particularly phenyl which is optionally substituted $C_{1-4}$ alkoxy group. Particularly, the compounds of the formula [I] wherein the optionally substituted aliphatic group of $R^2$ is the group of the formula: $R^4Y$ (wherein $R^4$ is an optionally substituted aromatic cyclic group and Y is an unsaturated aliphatic group which can form conjugated bonds with the thiazole ring of the thiazolopyridine ring) are preferred. Examples of the "aromatic ring" and "substituent" of "an optionally substituted aromatic cyclic group" represented by $R^4$ include those as described above with respect to $R^3$. Y is an alkyl group having 1 to 4 carbon atoms or an alkenyl group having 2 to 4 carbon atoms, such as —CH=CH—, —CH=CH—CH=CH— and the like. Further, the compounds wherein $R^1$ is hydrogen atom and $R^2$ is an optionally substituted phenyl group, or an alkenyl group conjugated with the thiazole ring having 2 to 4 carbon atoms which may be substituted with phenyl, thienyl, furyl, pyridyl, pyrazinyl or imidazolyl are preferred aspect from the viewpoint of the activities. Preferred examples of the optionally substituted alkenyl group represented by $R^2$ include vinyl and butadienyl which may be substituted with an optionally substituted phenyl or an optionally substituted imidazolyl.

The compounds of the formula [I] may have stereoisomers depending upon the kind of the substituents of $R^1$ and $R^2$. Not only these isomers alone, but also a mixture thereof are included in the scope of the present invention.

Salts of the compounds represented by the formula [I] are preferably pharmaceutically acceptable salts, and examples of the pharmaceutically acceptable salt include those formed with inorganic acids such as halogenated hydrogen (e.g., hydrogen chloride, hydrogen bromide, hydrogen fluoride, hydrogen iodide, etc.), phosphoric acid, sulfuric acid and the like and organic acids such as organic carboxylic acid (e.g., oxalic acid, phthalic acid, fumaric acid, maleic acid, etc.), sulfonic acids (e.g., methanesulfonic acid, benzenesulfonic acid, etc.) and the like. Further, when the compounds [I] contain acidic groups such as carboxyl group and the like as the substituents on $R^1$ and $R^2$, the salts include inorganic base salts formed with an alkaline metal (e.g., sodium, potassium, etc.) or alkaline earth metal (e.g., magnesium, etc.) as well as salts formed with an organic base (e.g., amines such as dicyclohexylamine, triethylamine, 2,6-lutidine, etc.).

Hereinafter, the compounds of the formula [I] and the salts thereof are merely referred to as the "compound [I]".

For example, the compound [I] of the present invention can be produced according to the process of the scheme I:

Scheme I

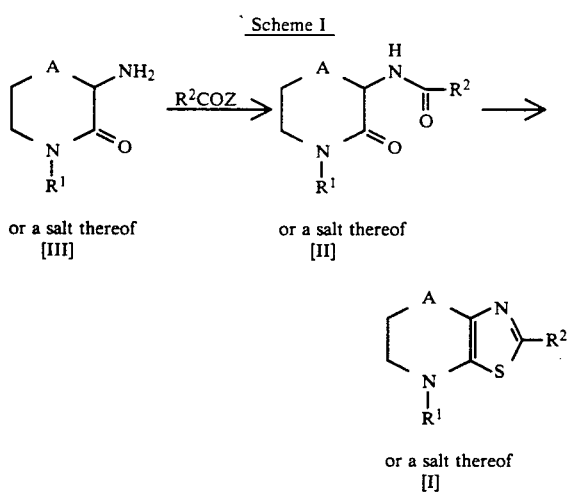

wherein A, $R^1$ and $R^2$ are as defined above and $R^2COZ$ is a reactive derivative of the corresponding carboxylic acid.

Namely, the compound [I] can be obtained by acylating the compound [III] or a salt thereof (examples of the salt include those as described above with respect to the salts of the compound [I] with a reactive derivative of carboxylic acid represented by the formula: $R^2COZ$ to obtain a compound [II], and then treating the compound [II] with a sulfurating agent. More particularly, as the reactive derivative of the formula: $R^2COZ$, for example, there are acid chlorides, acid bromides, imidazolides, anhydrides, acid azides, N-phthalimido esters, N-oxysuccinimide esters and the like. Further, instead of using the activated ester, a carboxylic acid of the formula: $R^2COOH$ may be directly reacted with the compound [III] in the presence of a coupling reagent such as N,N′-dicyclohexylcarbodiimide (hereinafter sometimes, abbreviated as DCC) and the like.

The reactive derivative of the formula: $R^2COZ$ is normally used in an amount of about 1 to 3 moles, preferably, about 1 to 1.2 moles per 1 mole of the compound [III]. When the carboxylic acid of the formula: $R^2COOH$ is reacted, the carboxylic acid is normally used in an amount of about 1 to 3 moles, preferably, about 1 to 1.2 moles per 1 mole of the compound [III] in the presence of about 1 to 1.2 moles of the coupling reagent per 1 mole of the compound [III].

Normally, the reaction proceeds smoothly with ice cooling or at a temperature of up to room temperature (the term "room temperature" used herein for explanation of the process means 5° to 35° C.). In this case, a solvent to be used may be any one which does not interfere with the reaction and is not specifically limited. Normally, chloroform, methylene chloride, tetrahydrofuran, dioxane, dimethylformamide or the like is used. When an acid chloride or acid bromide is used as the acylating agent, it is desirable to add an amine such as triethylamine, pyridine or the like to the reaction system. The reaction time varies according to a particular reagent, solvent, temperature and the like. Normally, the reaction time ranges from 30 minutes to 12 hours.

The reaction for converting the compound [II] to the compound [I] is conducted in the presence of a sulfurating agent such as phosphorous pentasulfide, Lawesson reagent or the like. In this case, the amount of the sulfurating agent to be used is normally about 1 to 3 moles, preferably, the equivalent mole per 1 mole of the compound [II]. As the reaction solvent, pyridine is preferred but there is no particular limitation. The reaction is conducted at a temperature of about 50° to 120° C., preferably, about 80° to 120° C. The reaction time varies depending upon the reaction temperature. Normally, the reaction time is about 3 to 12 hours and, when the reaction is conducted at about 100° to 120° C., the reaction may be completed within about 5 hours.

In the scheme I, the substituent represented by $R^1$ can be converted into another substituent represented by $R^1$ at any stage. Normally, it is advantageous that $R^1$ is converted into another group after the compound [I] is obtained. Examples of the conversion reaction of $R^1$ include those subjecting the compound [I] wherein $R^1$ is hydrogen atom to the conventional alkylation, sulfonylation or acylation to obtain the compound [I] wherein $R^1$ is an alkyl group, sulfonic acyl group or carboxylic acyl group.

These reaction can be conducted according to a known method, but they can be also conducted, for example, as follows:

In order to obtain the compound [I] wherein $R^1$ is a acyl group from the compound [I] wherein $R^1$ is hydrogen atom [hereinafter, sometimes, referred to as the compound [I] ($R^1$=H)], the compound [I] ($R^1$=H) can be acylated. In order to obtain the compound [I] wherein $R^1$ is a carboxylic acyl group, the reactive derivative of the carboxylic acyl can be reacted with the compound [I] ($R^1$=H). Regarding the kind of the reactive derivative of carboxylic acyl, reaction conditions and the like, those described above with respect to the reaction for obtaining the compound [II] from the compound [III] can be normally applied as they are. According to these conditions and the like, the reaction proceeds smoothly. In order to convert the compound [I] ($R^1$=H) into the compound [I] wherein $R^1$ is sulfonic acyl, the reaction of the compound [I] ($R^1$=H) with a sulfonyl halide is advantageous. Normally, the reaction is conducted in the presence of an amine such as triethylamine, pyridine or the like. The solvent to be used can be any one which does not interfered with the reaction. Preferably, acetone, dioxane, dimethylformamide, tetrahydrofuran, chloroform, methylene chloride or the like is used. In a particular case, pyridine can be used as a solvent. The reaction proceeds smoothly at 0° C. to room temperature and completes within 30 minutes to 5 hours. The amount of the amine to be used is about 1 to 3 moles per 1 mole of the compound [I], and the amount of the acylating agent is about 1 to 2 moles.

In order to obtain the compound [I] wherein $R^1$ is an alkyl group from the compound [I] wherein $R^1$ is hydrogen atom, the compound [I] ($R^1$=H) can be subjected to an alkylation reaction. As the alkylating agent to be used, for example, there are halogenated alkyl (examples of halogen include chlorine, bromine and iodine), alkyl esters of sulfonic acid (e.g., alkyl ester of p-toluenesulfonic acid, alkyl ester of methanesulfonic acid, etc.) and the like. The amount of the alkylating agent to be used is about 1 to 2 moles per 1 mole of the compound [I]. Normally, the reaction is conducted in the presence of an inorganic base such as potassium carbonate, sodium carbonate or the like, or an organic base such as triethylamine, pyridine or the like. The base can be used in the equivalent mole to the alkylating agent. The solvent to be used is not specifically limited and, for example, tetrahydrofuran, dioxane, dimethylformamide, dimethylacetoamide or the like is preferably used. Normally, the reaction can be conducted with heating, preferably, at about 30° to 100° C.

The compound [I] wherein $R^1$ is an alkyl group can be also obtained by the reduction of the compound [I] wherein $R^1$ is a carboxylic acyl group. The reduction can be conducted according to the conventional method, for example, by the reduction with a reducing agent such as lithium aluminum hydride, diborane or the like is suitable. In this case, as the solvent, ether, tetrahydrofuran or dioxane can be used. Normally, the reaction proceeds under reflux.

The compound [I] can also be produced according to other known methods or modification thereof.

Among the compounds [III] which are the starting compounds of the process of the present invention, those wherein $R^1$ is hydrogen atom are known compounds, and the compounds [III] wherein $R^1$ is other than hydrogen atom can be synthesized according to the process of the scheme II described by J. P. Snyder et al. [J. Med. Chem., 29, 251 (1986)]:

Scheme II

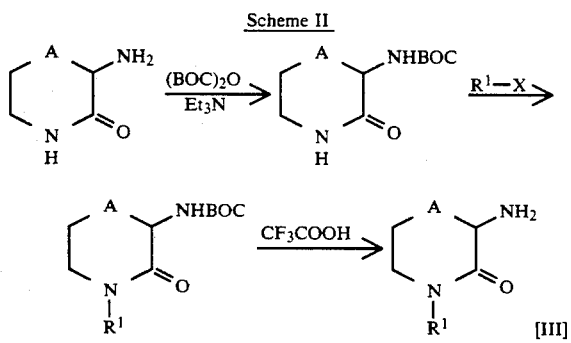

wherein A and $R^1$ are as defined above, Et is ethyl group, X is a halogen atom and BOC is tert-butoxycarbonyl group.

Further, according to the reaction for converting $R^1$ of the compound [I] into other groups as described above, the compound [III] wherein $R^1$ is other than hydrogen atom can be produced from the compound [III] wherein $R^1$ is hydrogen atom.

The compound [I] obtained according to the above process can be isolated and purified by the conventional separation means such as recrystallization, distillation, chromatography and the like. When the compounds [I] thus obtained are in the free form, they can be converted into salts by, for example, neutralization according to a known method. On the other hand, when the compounds [I] obtained are in the salt form, they can be converted into the free form.

The compounds [I] of the present invention have circulatory system improvement activities or antiallergic activities such as improvement of metabolism of poly unsaturated fatty acid esters (e.g., linolic acid, γ-linolenic acid, α-linolenic acid, arachidonic acid, dihomo-γ-linolenic acid, eicosapentaenoic acid, etc.), particularly, inhibitory activity for inhibitory lipoperoxide formation reaction (antioxidation activity); inhibitory activity for formation of 5-lipoxygenase metabolite [e.g., leukotrienes, 5-hydroperoxyeicosatetraenoic acid (HPETE), 5-hydroxyeicosatetraenoic acid (HETE), lipoxins, leukotoxines, etc. ]; inhibition of thromboxane $A_2$-synthetase; activity for retaining and enhancing prostaglandin $I_2$-synthetase; $LTD_4$ receptor antagonism; scavenging activity for active oxygen species and the like.

Among these activities, the compounds [I] of the present invention particularly tend to remarkably manifest lipoperoxide formation inhibitory activity (antioxidation activity).

The compounds [I] have low toxicity and little side effect.

Accordingly, the compounds [I] of the present invention have therapeutic and preventive effects on various diseases of mammal (e.g., mouse, rat, rabbit, dog, monkey, human, etc.) such as thrombosis due to platelet aggregation; ischemic diseases due to constriction of arterial vascular smooth muscle or vasospasm in the heart, lung, brain and kidney (e.g., cardiac infarction, cerebral apoplexy, etc.); neuropathy (e.g., Parkinson's diseases, Arzheimer's diseases, Lou-Gehring's diseases, muscular dystrophy, etc.); functional disorders caused by central damage such as cranial injury, spinal injury, etc.; dysmnesia or emotional disturbance (disorders accompanied by nerve cell necrosis caused by hypoxia, cerebral lesion, cerebral hemorrhage, cerebral infarction, cerebral thrombosis, etc.); convulsion and epilepsia caused after cerebral apoplexy, cerebral infarction, cerebral surgery or cranial injury; nephritis; pulmonmry insufficiency; bronchical asthma; inflammation; arterial sclerosis; atherosclerosis; hepatitis; acute hepatitis; cirrhosis; hepersensitivity pneumonitis; immune deficiency syndrome; circulatory diseases caused by injury of enzymes, tissue, cells, etc. of the living body due to active oxygen sepcies (e.g., superoxide, hydroxide radical, etc.) (e.g., cardiac infarction, cerebral apoplexy, cerebral edema, nephritis, etc.); tissue fibroplastic phenomenon; carcinogensis and the like. For example, the compounds [I] of the present invention are useful as medicines such as an antithrombotic drug, an antivasoconstriction drug, an antiasthmatic drug, an antiallergic drug, a drug for improving circulatory system such as the heart and brain, a drug for treating nephritis, a drug for treating hepatitis, a drug for inhibiting tissue fibroplastic, a drug for scavenging active oxygen species, a drug for regulating and improving aracidonate cascade substances and the like.

The compounds [I] can be orally or parenterally administered in safety as they are, or in the form of pharmaceutical compositions (e.g., tablets, capsules, solutions, injection preparations, suppositories, etc.) combined with known pharmaceutically acceptable carriers, excipient and the like. The dose varies depending upon a particular subject, administration route, conditions of diseases and the like. For example, in the case of administering orally to an adult patient with circulatory diseases, it is advantageous that the compounds of the present invention is normally administered 1 to 3 times per day with a daily dose of about 0.1 to 20 mg/kg, preferably, 0.2 to 10 mg/kg.

As described hereinabove, according to the present invention, there are provided the compounds having excellent lipoperoxide formation inhibitory and antioxidation activities, which are useful as medicines for preventing and treating circulatory diseases and allergic diseases of mammal and the like.

The following Experiments, Reference Examples and Examples further illustrate the present invention in detail but are not to be construed to limit the scope thereof.

EXPERIMENT 1

Effects of drugs on the excitatory behavior induced by spinal intrathecal injection of $FeCl_2$ in mice Male Slc:ICP mice (5 weeks) were used. Each group consisted of 10 mice. 5 μl of 50 mM $FeCl_2$ in saline was injected into spinal subarchnoid space between the 1st sacral and the 6th lumbar segment, the behavioral responses were observed from 15 min. to 1 hr. after the intrathecal injection of $FeCl_2$ and scored as follows.

| Score | Behavioral responses |
| --- | --- |
| 0: | normal (no abnormal behavior) |
| 1: | vigorously biting lower abdomen or lower extremities |
| 2: | a) extremely biting lower body with rolling<br>b) hyperreactivity and agressive to external stimuli<br>c) tremor<br>at least one of above three behavioral changes were observed |
| 3: | clonic convulsion |
| 4: | tonic convulsion or paralysis of lower extremities. |
| 5: | death |

The test compounds (100 mg/kg) were orally administered 30 min. prior to $FeCl_2$ injection. The mean scores and their percent inhibitions are shown in Table 1.

TABLE 1

| Example No. | Average score administration of compound (100 mg/kg) | administration of saline | Percent inhibition (%) |
| --- | --- | --- | --- |
| 1 | 0.8 | 4.6 | 82.6 |
| 2 | 0.7 | 4.7 | 85.1 |
| 3 | 0.9 | 4.7 | 80.9 |
| 5 | 0.4 | 4.6 | 91.3 |
| 6 | 0.1 | 4.7 | 97.9 |

As is clear from the above results, the compounds of the present invention have superior depressant activity of central nervous system disorders caused by formation of lipoperoxide due to ferrous chloride.

In the following Reference Examples and Example, elution of column chromatography was conducted with monitoring by TLC (thin layer chromatography). In the monitor by TLC, Kieselgel 60$F_{250}$ (70 to 230 mesh; manufactured by Merck Co.) was employed as the TLC plate. The developing solvent was the same as that used for elution of column chromatography and a UV detector was employed as the detection method. Kieselgel 60 (70 to 230 mesh) manufactured by Merck Co. was also used as silica gel for the column. The NMR spectrum was that of proton NMR and tertamethylsilane was used as the internal standard. The NMR spectrum was measured with VARIANEM 390 (90 MHz type spectrometer) and δ value was shown in ppm.

The abbreviations used in Examples are as follows:
s: singlet, br: broad, d: doublet, t: triplet, m: multiplet, dd: doublet of doublet, J: coupling constant, Hz: hertz, $CDCl_3$: dichloroform, $d_6$-DMSO: dimethylsulfoxide.

All the percents are by weight unless otherwise stated and "room temperature" is about 15° to 25° C.

REFERENCE EXAMPLE 1

3-(2,3-Dimethoxycinnamoyl)amino-δ-valerolactam

To a solution of 2,3-dimethoxycinnamic acid (5.0 g) in tetrahydrofuran (50 ml) was added N,N'-carbonyldiimidazole (4.28 g) and the mixture was stirred at room temperature for 30 minutes. To this was added 3-amino-δ-valerolactam (3.02 g), followed by stirring overnight. The reaction solution was diluted with chloroform and washed with a saturated soldium bicarbonate solution and then dried over anhydrous magnesium sulfate. The solvent was removed under reduced pressure and the residue was chromatographed on a silica gel column to obtain the titled compound (2.91 g, 39.8%).

Melting point: 164°-166° C. (recrystallized from ethanol-hexane).

IR (KBr) $cm^{-1}$: 3358, 1695, 1661, 1622, 1579, 1538, 1480, 1226, 1067, 797, 756.

NMR ($d_6$-DMSO) δ: 1.50-2.10 (4H, m), 3.17 (2H, brs), 3.76 (3H, s), 3.83 (3H, s), 4.29 (1H, m), 6.72 (1H, d, J=15.9 Hz), 7.12 (3H, m), 7.64 (1H, d, J=15.9 Hz), 7.66 (1H, m), 8.35 (1H, d, J=7.9 Hz).

Elemental analysis (%), Calcd. for $C_{16}H_{20}N_2O_4$: C, 63.14; H, 6.62; N, 9.20. Found: C, 63.45; H, 6.72; N, 9.07.

REFERENCE EXAMPLE 2

3-(3-Amino-4-methylbenzoyl)amino-δ-valerolactam

According to the same manner as that described in Reference Example 1, the titled compound was obtained from 3-amino-4-methylbenzoic acid and 3-amino-δ-valerolactam (yield: 56.3%).

Melting point: 161°-164° C. (recrystallized from ethyl acetate-hexane).

IR (KBr) $cm^{-1}$: 3358, 1675, 1645, 1575, 1539, 1495, 1455, 1424, 1333.

NMR ($d_6$-DMSO) δ:1.68-2.10 (4H, m), 3.16 (2H, brs), 4.31 (1H, m), 4.97 (2H, brs), 6.95-7.15 (3H, m), 7.61 (1H, brs), 8.22 (1H, d, J=8.1 Hz).

Elemental analysis (%), Calcd. for $C_{13}H_{17}N_3O_2$·0.3$H_2O$: C, 61.79; H, 7.02; N, 16.63. Found: C, 61.86; H, 7.11; N, 16.60.

REFERENCE EXAMPLE 3

3-(β-3-Indolylacryloyl)amino-δ-valerolactam

According to the same manner as that described in Reference Example 1, the titled compound was obtained from indole-3-acrylic acid and 3-amino-δ-valerolactam (yield: 63.8%).

Melting point: 231°-234° C. (recrystallized from ethyl acetate-ethanol).

IR (KBr) $cm^{-1}$: 3306, 3220, 1676, 1612, 1543, 1526, 1491, 1459, 1365, 1319, 1281, 809, 752.

NMR ($d_6$-DMSO-$D_2O$) δ: 1.54-2.15 (4H, m), 3.18 (2H, m), 4.31 (1H, m), 6.69 (1H, d, J=15.8 Hz), 7.19 (2H, m), 7.48 (1H, dd, J=2.2, 6.4 Hz), 7.60 (1H, m), 7.64 (1H, d, J=15.8 Hz), 7.75 (1H, s), 7.93 (1H, dd, J=1.8, 6.3 Hz), 8.21 (1H, d, J=8.0 Hz).

Elemental analysis (%), Calcd. for $C_{16}H_{17}N_3O_2$·0.3$H_2O$: C, 66.56; H, 6.14; N; 14.55. Found: C, 66.52; H, 6.25; N, 14.63.

REFERENCE EXAMPLE 4

3-{β-(1-Methylimidazole-4-yl)acryloyl}amino-δ-valerolactam

To a solution of β-(1-methylimidazole-4-yl)acrylrate hydrochloride (7 g, 37.1 mmole) in dimethylformamide (60 ml) was added triethylamine (7.51 g, 74.2 mmole) and 1-hydroxybenzotriazole hydrate (6.25 g, 40.8 mmole) and the mixture was ice-cooled, and then a solution of dicyclohexylcarbodiimide (8.42 g, 40.8 mmole) in dimethylformamide (15 ml) was added dropwise. After stirring at 80° C. for 30 minutes, followed by at room temperature for 30 minutes, 3-amino-δ- valerolactam (5.08 g, 44.5 mmole) was added to the reaction mixture which was heated with stirring for 13 hours. After cooling to room temperature, a sodium bicarbonate solution was added to the mixture which was extracted with a chloroform-methanol mixed solvent. After drying over magnesium sulfate, the solvent was removed under reduced pressure. The residue was subjected to silica gel flash chromatography and then recrystallized from ethanol/chloroform to obtain the titled compound (6.72 g, 73.0%).

Melting point: 280°-282° C. (recrystallized from ethyl acetate-ethanol).

IR (KBr) cm$^{-1}$: 3340, 1673, 1630, 1527, 1493, 1454, 1444

NMR (d$_6$-DMSO-D$_2$O) δ: 1.50–2.05 (4H, m), 3.65 (3H, s), 4.28 (1H, m), 6.54 (1H, d, J=15.3 Hz), 7.26 (1H, d, J=15.3 Hz), 7.39 (1H, s), 7.60 (1H, brs), 7.62 (1H, s), 8.20 (1H, d, J=8.3 Hz).

Elemental analysis (%),
Calcd. for C$_{12}$H$_{16}$N$_4$O$_2$.0.1H$_2$O: C, 57.63; H, 6.53; N, 22.40.
Found: C, 57.70; H, 6.77; N, 22.17.

REFERENCE EXAMPLE 5

3-{β-(1-Ethyl-2-phenylimidazole-4-yl)acryloyl}amino-δ-valerolactam

β-(1-Ethyl-2-phenylimidazole-4-yl)acrylate hydrochloride (5.49 g, 20.3 mmole) was heated with stirring in thionyl chloride (50 ml) for 50 minutes. After excessive thionyl chloride was completely distilled off under reduced pressure, tetrahydrofuran (50 ml) and triethylamine (4.12 g, 40.7 mmole) were added and then 3-amino-δ-valerolactam (2.79 g, 24.4 mmole) was added to the mixture with cooling, followed by stirring at room temperature overnight. A sodium bicarbonate solution was added to the reaction mixture which was extracted with a chlorofolm-methanol mixed solvent. After drying over magnesium sulfate, the solvent was distilled off under reduced pressure. The residue was subjected to silica gel flash chromatography to obtain the titled compound (29 g, 62.3%).

Melting point: 270°-272° C. (recrystallized from ethyl acetate-ethanol).

IR (KBr) cm$^{-1}$: 3338, 1680, 1652, 1633, 1509, 1474, 1446, 1361, 796.

NMR (d$_6$-DMSO) δ: 1.32 (3H, t, J=7.3 Hz), 1.50–2.07 (4H, m), 3.15 (2H, brs), 4.05 (2H, q, J=7.3 Hz), 4.27 (1H, m), 6.63 (1H, d, J=15.3 Hz), 7.30 (1H, d, J=15.3 Hz), 7.43–7.68 (7H, m), 8.20 (1H, d, J=8.1 Hz).

Elemental analysis (%), Calcd. for C$_{19}$H$_{22}$N$_4$O$_2$: C, 67.44; H, 6.55; N, 16.56. Found: C, 69.90; H, 6.55; N, 16.42.

REFERENCE EXAMPLE 6

3-(2-(4-Methoxyphenyl)propionylamino-δ-valerolactam

According to the same manner as that described in Reference Example 1, the title compound was obtained from 3-(4-methoxyphenyl)propionic acid and 3-amino-δ-valerolactam (yield: 86.3%).

Melting point: 184°-186° C. (recrystallized from ethyl acetate-ethanol).

IR (KBr) cm$^{-1}$: 3308, 1667, 1640, 1540, 1514, 1496, 1454, 1247, 1035, 822.

NMR (d$_6$-DMSO) δ: 1.43–2.00 (4H, m), 2.34 (2H, m), 2.75 (2H, m), 3.12 (2H, m), 3.71 (3H, s), 4.14 (1H, m), 6.81 (1H, d, J=8.7 Hz), 7.12 (1H, d, J=8.7 Hz), 7.58 (1H, brs), 8.02 (1H, d, J=8.1 Hz).

Elemental analysis (%), Calcd. for C$_{15}$H$_{20}$N$_2$O$_3$: C, 65.20; H, 7.30; N, 10.14. Found: C, 65.31; H, 7.53; N, 10.03.

EXAMPLE 1

2-(2,3-Dimethoxystyryl)-4,5,6,7-tetrahydrothiazolo[5,4-b]pyridine 3-(2,3-Dimethoxycinnamoyl)amino-δ-valerolactam (2.76 g) and phosphorous pentasulfide (2.02 g) were added to pyridine (20 ml) which was refluxed for 3 hours. After cooling, the reaction mixture was diluted with chloroform-methanol and washed with a saturated sodium bicarbonate solution and then dried over anhydrous magnesium sulfate. The solvent was distilled off under reduced pressure. The residue was subjected to silica gel column chromatography and recrystallized from ethyl acetate to obtain the titled compound (260 mg, 10.5%).

Melting point: 122°-124° C. (recrystallized from ethyl acetate).

IR (KBr) cm$^{-1}$: 3376, 1615, 1577, 1538, 1478, 1445, 1423, 1365, 1353, 1339, 1262, 1246, 1068, 960, 782

NMR (d$_6$-DMSO) δ: 1.86 (2H, m), 2.69 (2H, t, J=6.4 Hz), 3.18 (2H, m), 3.74 (3H, s), 3.81 (3H, s), 6.28 (1H, brs), 6.95 (1H, dd, J=1.4 Hz, 8.1 Hz), 7.05 (1H, t, J=7.9 Hz), 7.11 (1H, d, J=16.4 Hz), 7.21 (1H, d, J=16.4 Hz), 7.25 (1H, dd, J=1.4 Hz, 7.8 Hz).

Elemental analysis (%), Calcd. for C$_{16}$H$_{18}$N$_2$SO$_2$: C, 63.55; H, 6.00; N, 9.26; S, 10.60. Found: C, 63.66; H, 6.11; N, 9.22; S, 10.57.

EXAMPLE 2

2-(3-Amino-4-methylphenyl)-4,5,6,7-tetrahydrothiazolo[5,4-b]pyridine

According to the same manner as that described in Example 1, the titled compound was obtained from 3-(3-amino-4-methylbenzoyl)amino-δ-valerolactam and phosphorous pentasulfide (yield: 30.3%).

Melting point: 98°-101° C. (recrystallized from ethyl acetate-hexane)

IR (KBr) cm$^{-1}$: 3256, 1621, 1568, 1544, 1513, 1471, 1372, 1345, 1309, 866, 819.

NMR (CDCl$_3$O) δ: 1.99 (2H, m), 2.17 (3H, s), 2.86 (2H, t, J=6.4 Hz), 3.29 (2H, t, J=5.4 Hz), 3.67 (3H, brs), 7.00–7.20 (3H, m).

Elemental analysis (%), Calcd. for C$_{13}$H$_{15}$N$_3$S: C, 63.64; H, 6.16; N, 17.13; S, 13.07. Found: C, 63.36; H, 6.40; N, 16.78; S, 13.08.

EXAMPLE 3

2-(3-Amino-4-methylphenyl)-4,5,6,7-tetrahydrothiazolo[5,4-b]pyridine dihydrochloride 2-(3-Amino-4-methylphenyl)-4,5,6,7-tetrahydrothiazolo[5,4-b]pyridine was neutralized with hydrochloric acid and recrystallized from ethanol to obtain the titled compound (yield: 48.1%).

Melting point: 186°-189° C. (recrystallized from ethanol).

IR (KBr) cm$^{-1}$: 3438, 1602, 1523, 1480, 1466, 1348, 1282, 836.

NMR (d$_6$-DMSO-D$_2$O) δ: 1.93 (2H, m), 2.37 (3H, s), 2.77 (2H, t, J=6.2 Hz), 3.25 (2H, m), 7.39 (1H, d, J=8.1 Hz), 7.64 (1H, dd, J=1.7 Hz, 8.1 Hz), 7.84 (1H, d, J=1.7 Hz).

Elemental analysis (%), Calcd. for $C_{13}H_{15}N_3S.2HCl$; C, 49.06; H, 5.38; N, 13.20. Found: C, 49.48; H, 5.77; N, 13.23.

EXAMPLE 4

2-{2-(Indol-3-yl)ethenyl}-4,5,6,7-tetrahydrothiazolo[5,4-b]pyridine hydrochloride According to the same manner as that described in Example 1, the titled compound was obtained by reacting and refining 3-(β-3-indolylacryloyl)amino-δ-valerolactam and phosphorous pentasulfide and then neutralizing with hydrogen cholride (yield: 7.4%).

Melting point: 202°-205° C. (recrystallized from ethanol).

IR (KBr) cm$^{-1}$: 3218, 1596, 1572, 1528, 1455, 1404, 1355, 1334, 1284, 743.

NMR (CDCl$_3$) δ: 1.89 (2H, brs), 2.75 (2H, brs), 3.26 (2H, brs), 4.19 (1H, brs), 7.21 (2H, m), 7.30 (1H, d, J=16.2 Hz), 7.49 (1H, m), 7.70 (1H, d, J=16.2 Hz), 7.81-8.00 (2H, m), 11.88 (1H, s).

Elemental analysis (%), Calcd. for $C_{16}H_{15}N_3S.HCl$: C, 60.46; H, 5.07; N, 13.22; S, 10.09; Cl, 11.15. Found: C, 60.37; H, 5.05; N, 13.16; S, 10.19; Cl, 11.29.

EXAMPLE 5

2-{2-(1-Methylimidazole-4-yl)ethenyl}-4,5,6,7-tetrahydrothiazolo[5,4-b]pyridine dihydrochloride According to the same manner as that described in Example 1, the titled compound was obtained by reacting and refining 3-{β-(1-methylimidazole-4-yl)acryloyl}amino-δ-valerolactam and phosphorous pentasulfide and then neutralizing with hydrogen chloride (yield: 14.1%).

Melting point: 184°-187° C. (recrystallized from ethanol-chloroform).

IR (KBr) cm$^{-1}$: 3410, 1635, 1598, 1521, 1471, 1446, 1350, 837.

NMR (CDCl$_3$) δ: 1.89 (2H, m), 2.74 (2H, t, J=6.3 Hz), 3.24 (2H, t, J=5.0 Hz), 3.86 (3H, s), 4.46 (1H, brs), 7.03 (1H, d, J=16.5 Hz), 7.47 (1H, d, J=16.5 Hz), 7.81 (1H, s).

Elemental analysis (%), Calcd. for $C_{12}H_{14}N_4S.2HCl.0.5H_2O$: C, 43.91; H, 5.22; N, 17.07; S, 9.77; Cl, 21.60. Found: C, 43.90; H, 5.34; N, 16.67; S, 10.06; Cl, 21.63.

EXAMPLE 6

2-{2-(1-Ethyl-2-phenylimidazole-4-yl)ethenyl}-4,5,6,7-tetrahydrothiazolo[5,4-b]pyridine According to the same manner as that described in Example 1, the titled compound was obtained from 3-{β-(1-ethyl-2-phenylimidazole-4-yl)acryloyl}amino-δ-valerolactam and phosphorous pentasulfide and then neutralizing with hydrogen chloride (yield: 8.4%).

Melting point: 140°-142° C. (recrystallized from ethyl acetate).

IR (KBr) cm$^{-1}$: 3234, 1628, 1552, 1538, 1446, 1371, 1344, 1283, 821.

NMR (CDCl$_3$) δ: 1.41 (3H, t, J=7.3 Hz), 1.97 (2H, m), 2.82 (2H, t, J=6.4 Hz), 3.27 (2H, t, J=5.4 Hz), 4.02 (2H, q, J=7.3 Hz), 7.08 (1H, d, J=16.0 Hz), 7.10 (1H, s), 7.24 (1H, d, J=16.0 Hz), 7.41-7.52 (3H, m), 7.53-7.64 (2H, m).

Elemental analysis (%), Calcd. for $C_{19}H_{20}N_4S$: C, 67.83; H, 5.99; N, 16.65; S, 9.53. Found: C, 67.59; H, 5.98; N, 16.26; S, 9.51.

EXAMPLE 7

2-(2,3-Dimethoxystyryl)-4,5,6,7-tetrahydrothiazolo[5,4-b]pyridine dihydrochloride 2-(2,3-Dimethoxystyryl)-4,5,6,7-tetrahydrothiazolo[5,4-b]pyridine was neutralized with hydrochloric acid and recrystallized from ethanol-diethyl ether to obtain the title compound (yield: 92.7%).

Melting point: 174°-177° C. (recrystallized from ethanol-diethyl ether).

IR (KBr) cm$^{-1}$: 2546, 1626, 1609, 1592, 1574, 1478, 1443, 1431, 1345, 1272, 1066, 795.

NMR (d$_6$-DMSO-D$_2$O) δ: 1.93 (2H, t, J=4.9 Hz), 2.79 (2H, t, J=6.1 Hz), 3.30 (2H, t, J=4.8 Hz), 3.79 (3H, s), 3.84 (3H, s), 7.08 (1H, brd, J=8.8 Hz), 7.16 (1H, d, J=8.1 Hz), 7.28 (1H, brd, J=7.4 Hz), 7.36 (1H, d, J=16.5 Hz), 7.48 (1H, d, J=16.5 Hz)

Elemental analysis (%), Calcd, for $C_{16}H_{18}N_2SO_2.2HCl$: C, 51.20; H, 5.37; N, 7.46; S, 8.54; Cl, 18.89. Found: C, 52.11; H, 5.41; N, 7.46; S, 8.97; Cl, 18.41.

EXAMPLE 8

2-{(2-(1-Ethyl-2-phenylimidazol-4-yl)ethenyl}-4,5,6,7-tetrahydrothiazolo[5,4-b]pyridine dihydrochloride 2-{2-(1-Ethyl-2-phenylimidazol-4-yl)ethenyl}-4,5,6,7-tetrahydrothiazolo[5,4-b]pyridine was neutralized with hydrochloric acid and recrystallized from ethanoldiethyl ether to obtain the title compound (yield: 94.2%).

Melting point: 181°-184° C. (recrystallized from ethanol-diethyl ether).

IR (KBr) cm$^{-1}$: 3420, 1586, 1532, 1480, 1464, 1340.

NMR (d$_6$-DMSO) δ: 1.41 (3H, t, J=7.3 Hz), 1.89 (2H, m), 2.74 (2H, t, J=6.2 Hz), 3.24 (2H, t, J=5.0 Hz), 4.17 (2H, q, J=7.3 Hz), 5.22 (1H, brs), 7.01 (1H, d, J=16.4 Hz), 7.55 (1H, d, J=16.4 Hz), 7.62-7.75 (3H, m,) 7.78-7.88 (2H, m), 8.09 (1H, s).

Elemental analysis (%), Calcd. for $C_{19}H_{20}N_4S.2HCl.0.5H_2O$: C, 54.54; H, 5.54; N, 13.39; S, 7.66; Cl, 16.95. Found: C, 54.70; H, 5.60; N, 13.37; S, 7.80; Cl, 16.83.

EXAMPLE 9

4-Acetyl-2-(2,3-dimethoxystyryl)-4,5,6,7-tetrahydrothiazolo[5,4-b]pyridine to a solution of 2-(2,3-dimethoxystyryl)-4,5,6,7-tetrahydrothiazolo[5,4-b]pyridine (1.0 g, 3.3 mmole) in pyridine (10 ml) was added dropwise acetic anhydride (0.68 g, 6.6 mmole) with ice-cooling. The reaction mixture was heated with stirring at 80° C. for 3 hours and then a sodium bicarbonate solution was added to the mixture which was extracted with a chloroform-methanol mixed solvent. The extract was dried over magnesium sulfate and concentrated. The residue was purified by flash column chromatography and then recrystallized from hexane-ethyl acetate to obtain the title compound (867 mg, yield: 76.0%).

Melting point: 185°-187° C. (recrystallized from hexane-ethyl acetate).

IR (KBr) cm$^{-1}$: 1651, 1593, 1575, 1536, 1478, 1446, 1273, 1065, 962, 785, 762.

NMR (CDCl$_3$) δ: 2.16 (2H, m), 2.34 (3H, s), 2.95 (2H, t, J=6.3 Hz), 3.87 (8H, m), 6.86 (1H, dd, J=1.4 Hz, 8.0 Hz), 7.06 (1H, t, J=8.1 Hz), 7.16-7.33 (2H, m), 7.61 (1H, d, J=16.5 Hz).

Elemental analysis (%), Calcd. for $C_{18}H_{20}N_2SO_3$: C, 62.77; H, 5.85; N, 8.13; S, 9.31. Found: C, 62.67; H, 5.79; N, 8.12; S, 9.45.

EXAMPLE 10

2-(2,3-Dimethoxystyryl)-4-methanesulfonyl-4,5,6,7-tetrahydrothiazolo[5,4-b]pyridine To a solution of 2-(2,3-dimethoxystyryl)-4,5,6,7-tetrahydrothiazolo[5,4-b]pyridine (1.0 g, 3.3 mmole) in pyridine (10 ml) was added dropwise methanesulfonyl chloride (0.45 g, 3.97 mmole) with ice-cooling. The reaction mixture was heated with stirring at room temperature for 3 hours and then a sodium bicarbonate solution was added to the mixture which was extracted with a chloroform-methanol mixed solvent. The extract was dried over magnesium sulfate and concentrated. The residue was purified by flash column chromatography and recrystallized from hexane-ethyl acetate to obtain the title compound (1.09 g, yield: 92.7%).

Melting point: 134°–136° C. (recrystallized from hexane-ethyl acetate).

IR (KBr) cm$^{-1}$: 1623, 1577, 1535, 1472, 1445, 1348, 1338, 1261, 1155, 1085, 970, 808, 760.

NMR (CDCl$_3$) δ: 2.09 (2H, m), 2.09 (2H, t, J=6.5 Hz), 2.98 (3H, s), 3.83 (2H, m), 3.87 (3H, s), 3.88 (3H, s), 6.88 (1H, dd, J=1.6 Hz, 8.0 Hz), 7.06 (1H, t, J=7.9 Hz), 7.17 (1H, dd, J=1.6 Hz, 7.9 Hz), 7.21 (1H, d, J=16.5 Hz), 7.56 (1H, d, J=16.5 Hz).

Elemental analysis (%), Calcd. for $C_{17}H_{20}N_2S_2O_4$: C, 53.66; H, 5.30; N, 7.36; S, 16.86. Found: C, 53.71; H, 5.42; N, 7.58; S, 16.85.

EXAMPLE 11

2-(2,3-Dimethoxystyryl)-4-(2-dimethylaminoethyl)-4,5,6,7-tetrahydrothiazolo[5,4-b]pyridine dihydrochloride 2-(2,3-Dimethoxystyryl)-4,5,6,7-tetrahydrothiazolo[5,4-b]pyridine (1.0 g, 3.3 mmole) and powdery potassium carbonate (1.37 g, 9.92 mmole) were suspended in dimethylformamide (20 ml). To the suspension was added N,N-dimethylaminoethyl chloride hydrochloride (0.57 g, 3.97 mmole) and the mixture was heated with stirring at 90° C. for 4 hours. Water was added to the mixture and an organic substance was extracted with a chloroform-methanol mixed solvent. The extract was dried over magnesium sulfate and concentrated. The residue was purified by flash column chromatography. The resulting oily compound was neutralized with hydrochloric acid and recrystallized from diethyl ether-ethanol to obtain the title compound (870 mg, yield: 54.4%).

Melting point: 118°–121° C. (recrystallized from diethyl ether-ethanol).

IR (KBr) cm$^{-1}$: 2694, 1692, 1602, 1576, 1505, 1480, 1344, 1271, 1190, 1064, 790, 750

NMR (d$_6$-DMSO) δ: 2.02 (2H, m), 2.79 (2H, m), 2.81 (3H, s), 2.83 (3H, s), 3.47 (2H, m), 3.78 (3H, s), 3.83 (3H, s), 3.92 (2H, m), 4.54 (2H, m), 7.02 (1H, dd, J=1.8 Hz, 8.1 Hz), 7.09 (1H, t, J=7.8 Hz), 7.33 (1H, dd, J=1.8 Hz, 7.6 Hz), 7.34 (1H, d, J=16.4 Hz), 7.54 (1H, d, J=16.4 Hz).

Elemental analysis (%), Calcd. for $C_{20}H_{27}N_3SO_2.2HCl.2H_2O$: C, 49.79; H, 6.89; N, 8.71; S, 6.65; Cl, 14.70. Found: C, 49.33; H, 6.41; N, 8.21; S, 6.62; Cl, 14.37.

EXAMPLE 12

2-{2-(4-Methoxyphenyl)ethyl}-4,5,6,7-tetrahydrothiazolo[5,4-b]pyridine

According to the same manner as that described in Example 1, the title compound was obtained from 3-{2-(4-methoxyphenyl)ethyl}carbonylamino-δ-valerolactum and phosphorous pentasulfide (yield: 21.5%).

Melting point: 89°–91° C. (recrystallized from petroleum ether-diethyl ether).

IR (KBr) cm$^{-1}$: 2952, 1610, 1558, 1513, 1490, 1443, 1350, 1303, 1282, 1242, 1034, 815.

NMR (CDCl$_3$) δ: 1.94 (2H, m), 2.78 (2H, t, J=6.4 Hz), 2.95 (2H, m), 3.10 (2H, m), 3.24 (2H, t, J=5.4 Hz), 3.79 (3H, s), 6.83 (1H, d, J=8.6 Hz), 7.14 (1H, d, J=8.6 Hz).

Elemental analysis (%), Calcd. for $C_{15}H_{18}N_2SO$: C, 65.66; H, 6.61; N, 10.21; S, 11.65. Found: C, 65.42; H, 6.60; N, 10.03; S, 11.73.

What is claimed is:

1. A compound of the formula:

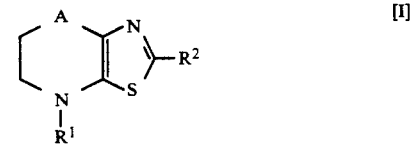

[I]

wherein A is a single bond or CH$_2$; R$^1$ is a hydrogen atom, or an optionally substituted alkyl, cycloalkyl, alkenyl, alkynyl, carboxylic acyl, or sulfonic acyl group; and R$^2$ is hydrogen atom, or an optionally substituted aromatic carbocyclic, aromatic heterocyclic, alkyl, cycloalkyl, alkenyl or alkynyl group, or a salt thereof.

2. A compound according to claim 1, wherein R$^1$ is hydrogen atom or an optionally substituted carboxylic acyl group.

3. A compound according to claim 1, wherein R$^2$ is an optionally substituted alkenyl group having 2 to 4 carbon atoms.

4. A compound according to claim 1, wherein R$^2$ is an optionally substituted aromatic carbocyclic or aromatic heterocyclic group.

5. A compound according to claim 1, wherein R$^1$ is hydrogen atom; and R$^2$ is an optionally substituted aromatic carbocyclic group, aromatic heterocyclic group or an alkenyl group having 2 to 4 carbon atoms substituted with an optionally substituted aromatic carbocyclic or aromatic heterocyclic group.

6. A compound according to claim 5, wherein A is CH$_2$, R$^1$ is hydrogen atom and R$^2$ is an alkenyl group having 2 to 4 carbon atoms substituted with a substituted aromatic carbocyclic group.

7. A compound according to claim 6, wherein A is CH$_2$, R$^1$ is hydrogen atom; and R$^2$ is an alkenyl having 2 to 4 carbon atoms substituted with a substituted C$_{6-10}$ aryl, C$_{3-8}$ cycloalkyl or C$_{7-14}$ aralkyl group.

8. A compound according to claim 5, wherein A is CH$_2$, R$^1$ is hydrogen atom and R$^2$ is an alkenyl group having 2 to 4 carbon atoms substituted with a substituted aromatic heterocyclic group.

9. A compound according to claim 5, wherein A is CH$_2$, R$^1$ is hydrogen atom; and R$^2$ is an alkenyl group having 2 to 4 carbon atoms substituted with a substituted 5 to 6 membered aromatic heterocyclic group containing 1 to 2 hetero atoms.

10. A compound according to claim 1, wherein $R^1$ is hydrogen atom; and $R^2$ is an substituted $C_{6-10}$ aryl, $C_{3-8}$ cycloalkyl or $C_{7-14}$ aralkyl group.

11. A compound according to claim 3 which is 2-(2,3-dimethoxystyryl)-4,5,6,7-tetrahydrothiazolo[5,4-b]pyridine or its salt.

12. A compound according to claim 4 which is 2-(3-amino-4-methylphenyl)-4,5,6,7-tetrahydrothiazolo[5,4-b]pyridine or its salt.

13. A compound according to claim 3 which is 2-{2 (indol-3-yl)ethenyl}-4,5,6,7-tetrahydrothiazolo[5,4-b]pyridine or its salt.

14. A compound according to claim 3 which is 2-{2-(1-methyl-imidozol-4-yl)ethenyl}-4,5,6,7-tetrahydrothiazolo[5,4-b]-pyridine or its salt.

15. A compound according to claim 3 which is 2-{2-(2-phenylimidazol-4-yl)ethenyl}-4,5,6,7-tetrahydro thiazolo[5,4-b]pyridine or its salt.

16. A compound according to claim 3 which is 2-{2-(1-ethyl-2-phenylimidazol-4-yl)ethenyl}-4,5,6,7-tetrahydro thiazolo[5,4-b]pyridine or its salt.

17. A pharmaceutical composition for inhibition of lipoperoxide formation which comprises the compound [I] of claim 1 or a pharmaceutically acceptable salt thereof, and a pharmaceutically acceptable carrier.

18. A pharmaceutical composition for inhibiting lipoxygenase which comprises the compound [I] of claim 1 or a pharmaceutically acceptable salt thereof, and a pharmaceutically acceptable carrier.

19. A pharmaceutical composition for treating ischemic diseases which comprises the compound [I] of claim 1 or a pharmaceutically acceptable salt thereof, and a pharmaceutically acceptable carrier.

20. A method for inhibition of lipoperoxide formation in a mammal in need thereof which comprises administering an effective amount of the compound [I] of claim 1 or a pharmaceutically acceptable salt.

21. A method for inhibiting lipoxygenase in a mammal in need thereof which comprises administering an effective amount of the compound [I] of claim 1 or a pharmaceutically acceptable salt thereof.

22. A method for treating ischemic diseases in a mammal in need thereof which comprises administering an effective amount of the compound [I] of claim 1 or a pharmaceutically acceptable salt thereof.

* * * * *